(12) United States Patent
Faccioli et al.

(10) Patent No.: US 10,981,127 B2
(45) Date of Patent: Apr. 20, 2021

(54) MIXING GROUP AND METHOD FOR MIXING TWO COMPOUNDS

(71) Applicant: TECRES S.p.A., Sommacampagna (IT)

(72) Inventors: Giovanni Faccioli, Monzambano (IT); Renzo Soffiatti, Nogara (IT)

(73) Assignee: TECRES S.P.A., Sommacampagna (IT)

( * ) Notice: Subject to any disclaimer, the term of this patent is extended or adjusted under 35 U.S.C. 154(b) by 462 days.

(21) Appl. No.: 15/564,092

(22) PCT Filed: Apr. 15, 2016

(86) PCT No.: PCT/IB2016/052151
§ 371 (c)(1),
(2) Date: Oct. 3, 2017

(87) PCT Pub. No.: WO2016/166711
PCT Pub. Date: Oct. 20, 2016

(65) Prior Publication Data
US 2018/0133668 A1 May 17, 2018

(30) Foreign Application Priority Data

Apr. 17, 2015 (IT) .................. 102015000012246

(51) Int. Cl.
*B01F 13/00* (2006.01)
*B01F 11/00* (2006.01)
(Continued)

(52) U.S. Cl.
CPC ...... *B01F 13/0023* (2013.01); *B01F 11/0054* (2013.01); *B01F 15/00506* (2013.01);
(Continued)

(58) Field of Classification Search
CPC ............... B01F 13/002; B01F 13/0023; B01F 11/0054; B01F 15/00506; B01F 2215/0029; A61B 2017/8838
See application file for complete search history.

(56) References Cited

U.S. PATENT DOCUMENTS 4,014,330 A * 3/1977 Genese ............... A61M 5/2429
604/88
5,193,907 A 3/1993 Faccioli et al.
(Continued)

FOREIGN PATENT DOCUMENTS

EP 1912597 4/2008
IT 1236864 4/1993
(Continued)

OTHER PUBLICATIONS

International Search Report dated Aug. 26, 2016 for PCT/IB2015/052151 (3 pages).
Written Opinion of the International Search Report (5 pages).

*Primary Examiner* — Anshu Bhatia
(74) *Attorney, Agent, or Firm* — Tutunjian & Bitetto, P.C.

(57) ABSTRACT

Mixing group for mixing two compounds to obtain a mixture, such as bone cement or an acrylic resin or a hydraulic cement, including:
a first component having a substantially tubular body and delimiting a first housing zone of a first compound to be mixed, the first component having a first end as well as a second end,
a second component with substantially tubular body and delimiting a second housing zone, the second component having a third end as well as a fourth end, the second component being set to contain a second compound to be mixed or a vial for containing a second compound to be mixed, (Continued)

the first housing zone being in fluid communication with the second housing zone, so as to allow the passage of the second compound from the second housing zone to the first housing zone.

20 Claims, 9 Drawing Sheets

(51) Int. Cl.
  *B01F 15/00* (2006.01)
  *A61B 17/88* (2006.01)
(52) U.S. Cl.
  CPC ............... *A61B 2017/8838* (2013.01); *B01F 2215/0029* (2013.01)

(56) References Cited

U.S. PATENT DOCUMENTS

| | | | |
|---|---|---|---|
| 5,478,337 A | * | 12/1995 | Okamoto ............. A61J 1/2089 604/413 |
| 5,569,191 A | | 10/1996 | Meyer |
| 8,465,197 B2 | | 6/2013 | Faccioli et al. |

FOREIGN PATENT DOCUMENTS

| | | |
|---|---|---|
| WO | 2006/123205 | 11/2006 |
| WO | 2011/809480 | 7/2011 |

* cited by examiner

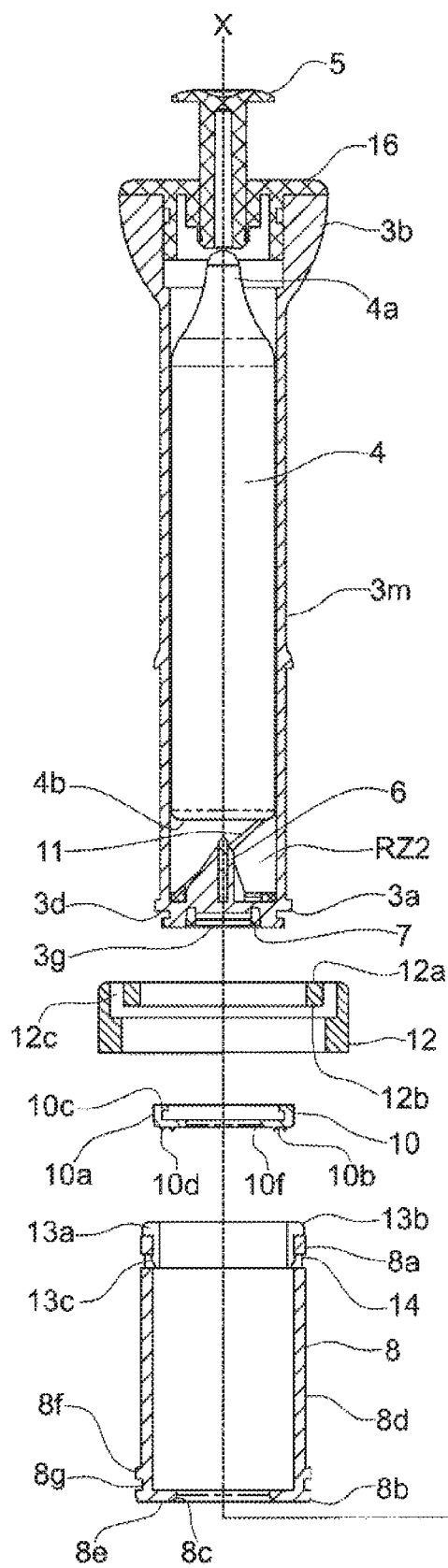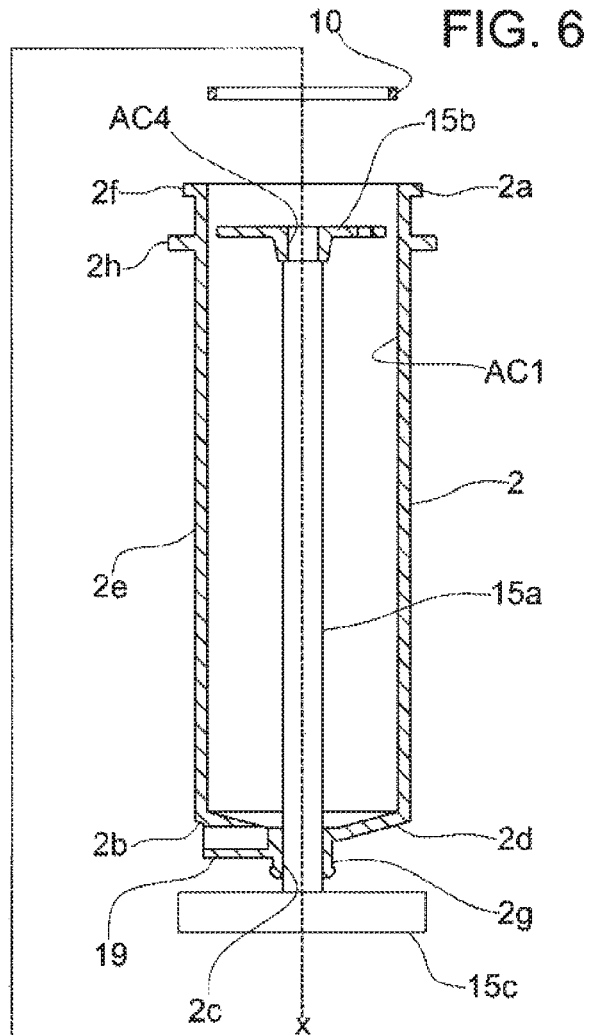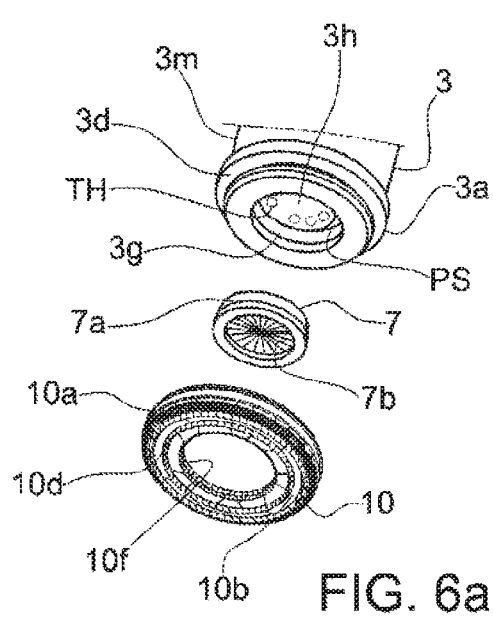
FIG. 6
FIG. 6a

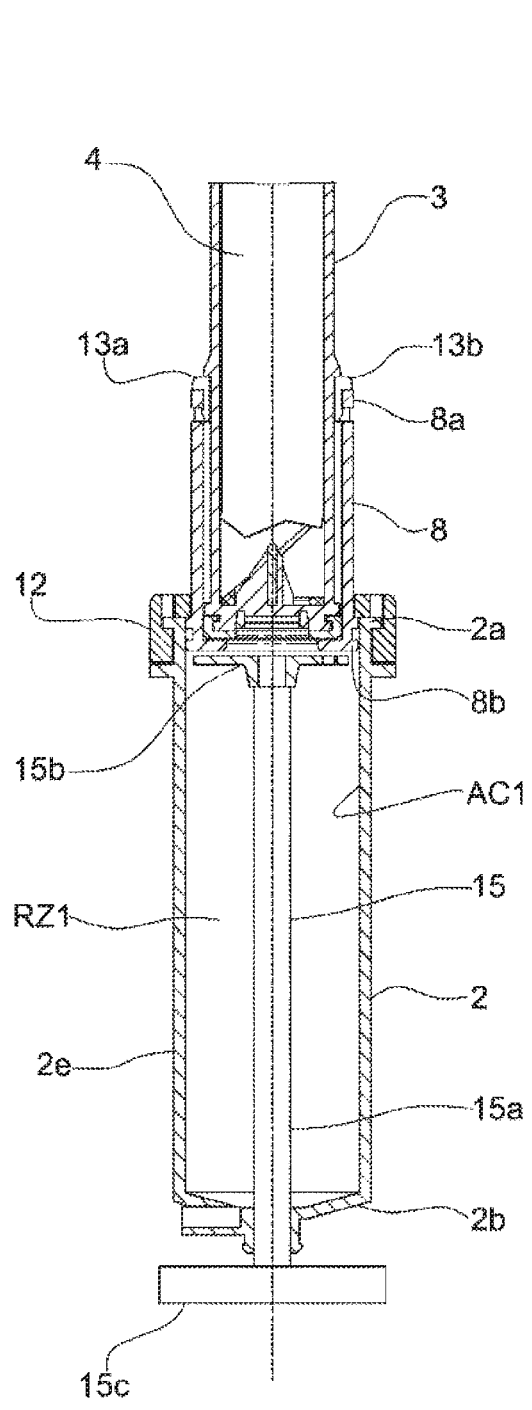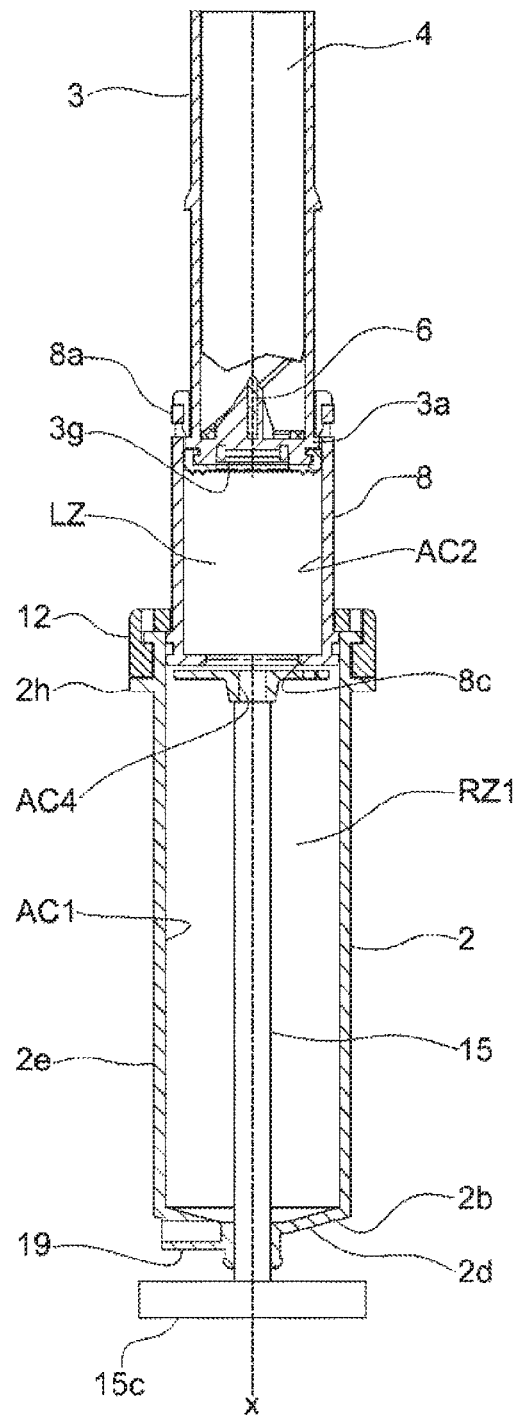

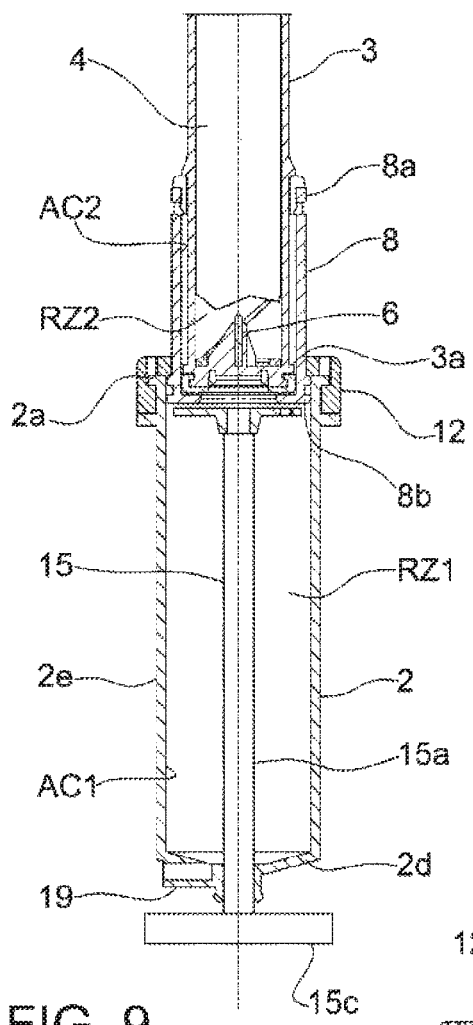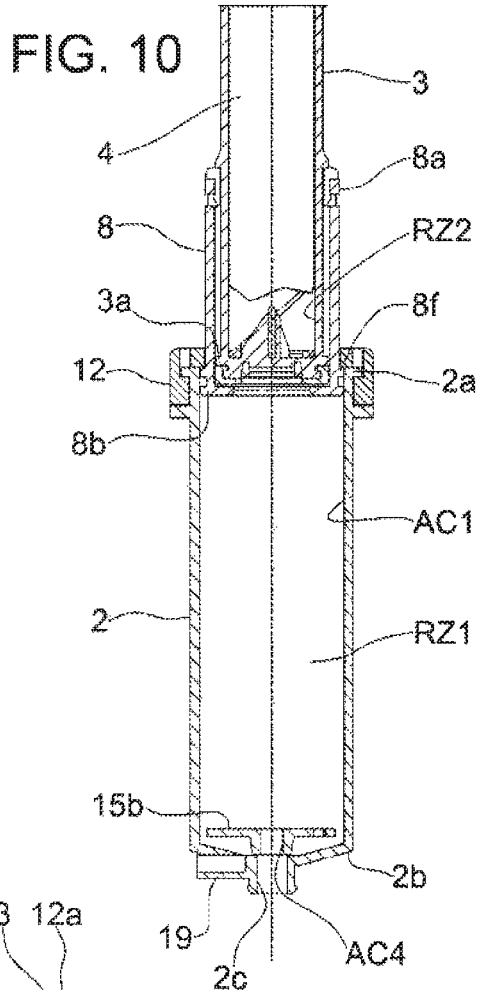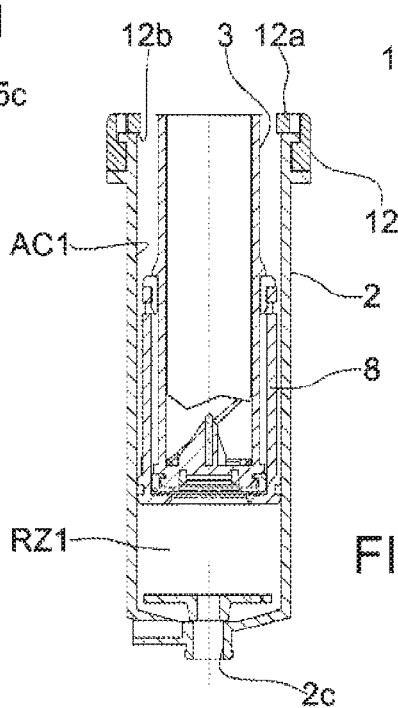

MIXING GROUP AND METHOD FOR
MIXING TWO COMPOUNDS

CROSS-REFERENCE TO RELATED APPLICATIONS

This application is a U.S. National Stage of International Application No. PCT/IB2016/052151 filed Apr. 15, 2016, which claims priority from IT 102015000012246 filed Apr. 17, 2015.

TECHNICAL FIELD OF THE INVENTION

The present invention regards a mixing group for mixing two compounds, such as a liquid and a powder for obtaining bone cement, as well as a method for mixing two compounds.

STATE OF THE PRIOR ART

Many types of liquid-powder mixers have been proposed for obtaining bone cement.

The Italian patent No. 1236864 along with the European patent No. 1912597, both on behalf of the applicant of the present patent application, teach a mixer comprising a first component delimiting a powder containment chamber, in which a second component is slidably mounted defining a housing zone for a vial containing liquid to be mixed with the powder.

In the powder containment chamber, a stem is then slidably mounted supporting a mixing component, while on the internal end, internal during use, of the second component a cap is mounted delimiting an annular groove for housing a gasket, the internal end of the cap delimiting a shoulder directed away from the containment chamber and intended to be abutted against a respective shoulder of the first component.

With such devices, the vial is broken, the movement of the second component is manually determined so as to exit from the first component, thus causing the entrance of the liquid of the broken vial into the powder containment chamber; then, the mixing is executed within the latter chamber until bone cement is attained. If desired, during the movement of the second component, a vacuum is applied in the powder containment chamber in order to facilitate the transfer of the liquid into the latter.

With such devices, it is very difficult to achieve a good seal of the powder containment chamber, considering the fact that the gasket, having to allow the manual movement of the second component with respect to the first, cannot be excessively hard or strong.

For such purpose, during the mixing of powder and liquid, there can be an entrance of air at the gasket and hence the formation of bubbles in the final bone cement mixture, which clearly would reduce the quality of the obtained bone cement.

In addition, the abovementioned devices have a volume of the first component that is much greater than that of the vial, in particular as a function of the configuration of the cap and of the other components of the respective device. As will be understood, this involves, for the devices according to the state of the art, an excessive final volume or width.

U.S. Pat. Nos. 4,014,330A, 5,569,191A, WO2011089480A1 and WO2006123205A1 teach respective solutions according to the state of the art.

SUMMARY OF THE INVENTION

One object of the present invention is to provide a new mixing group for mixing two compounds, in particular a liquid and a powder for obtaining bone cement.

Another object of the present invention is to provide a new mixing group which ensures a good seal of the housing zones of the compounds to be mixed.

Another object of the present invention is to provide a new mixing group which allows applying a good depression in order to push the liquid into the containment zone for the powder, without running the risk of causing the entrance of air into the latter and hence which allows reducing the risk of forming bubbles in the obtained final cement.

Another object of the present invention is to provide a new mixing group which allows applying a good depression during the mixing of liquid and powder, without running the risk of causing the entrance of air into the latter and, therefore, which allows reducing the risk of forming bubbles in the obtained final cement.

Another object of the present invention is to provide a new mixing group with limited size with respect to conventional groups.

Another object of the present invention is to provide a new mixing method due to which it is possible to mix two compounds, such as a liquid and a powder, in a quick and effective manner.

In accordance with one aspect of the invention, a mixing group is provided according to the present application.

In accordance with another aspect of the invention, a mixing method is provided according to the present application.

The present application refers to preferred and advantageous embodiments of the invention.

BRIEF DESCRIPTION OF THE DRAWINGS

Other characteristics and advantages of the invention will be more evident from the description of embodiments of a mixing group, illustrated as an example in the enclosed drawings, in which:

FIG. 6 is a view of the components of FIG. 5, separated;

FIG. 6a is a slightly bottom and exploded perspective view of some components of the group of FIG. 1;

FIGS. 7 to 11 are views similar to FIG. 5 of respective steps of a mixing method according to the present invention;

In the enclosed drawings, equivalent parts or components are marked with the same reference numbers.

DETAILED DESCRIPTION OF THE INVENTION

Figure 1:
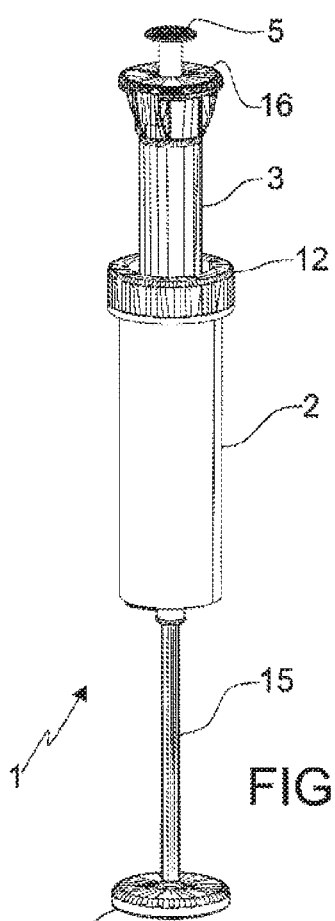
FIG. 1 is a slightly top perspective view of the mixing group according to the present invention.

First, with reference to FIGS. 1 to 11, a mixing group 1 is illustrated for mixing two compounds to obtain a mixture, such as a liquid (such as a monomer) and a powder (such as one or more polymers, possibly acrylic) for obtaining bone cement or an acrylic resin. The powder could also be inorganic with base of Calcium Salts, such as Calcium Sulfate (plaster) or mixtures of Tricalcium Phosphate (TCP) or Hydroxyapatite (HA) or mixtures with base of Calcium Oxides (CaO), Magnesium Oxides (MgO), Aluminum Oxides ($Al_2O_3$), Silicon Oxides ($SiO_2$), Iron Oxides ($Fe_2O_3$) and/or other complex Salts such as Calcium Metasilicates ($CaSiO_3$ and $Ca_2Si_2O_5$) and/or Tricalcium Aluminate $Ca_3(AlO_3)_2$ and/or Tetracalcium Aluminoferrite ($C_4AlFe$) and/or other inorganic compounds which—when joined with a second compound, such as pure water or an aqueous solution containing inorganic Salts synergistic with those present in the powder—give rise to a hardening mass commonly identifiable as "hydraulic cement". Preferably, all the compounds will possess a high grade of purity, such that the mixture gives rise to a biocompatible product or mixture.

The group comprises a first component or cylinder 2 having a substantially tubular body and delimiting a first housing zone RZ1 of a first compound to be mixed, such as a powder. More particularly the first component 2 delimits a first channel AC1 which is a through channel; as will be clearer hereinbelow, a first housing zone RZ1 of a first compound to be mixed is delimited in such channel, and the volume of such zone RZ1 is variable.

More particularly, the first component 2 has a first end 2a, as well as a second end 2b, if desired for supplying bone cement, which can delimit an opening or through hole 2c, if desired also for the passage of a stem of a mixer, which will be clearer hereinbelow. For such purpose, the second end 2b can terminate with a hollow shank section 2g for guiding the stem, in any case ensuring the fluid seal or better yet powder and cement seal of the through hole 2c.

The substantially tubular body of the first component 2 extends around an axis of symmetry x-x, for example it can comprise a solid of revolution around an axis of symmetry x-x and it can have from one side—during use proximal to the second end 2b—to a side distal from the latter a substantially frustoconical section with progressively increasing diameter 2d, then a substantially cylindrical section 2e terminating with the first end 2a.

Teeth or tabs 2f can then be provided, extended outward from the first end 2a and angularly offset from each other, e.g. four teeth 2f offset 90° from each other.

Starting from an external portion of the substantially cylindrical section 2e, a crown element 2h can also be extended, if desired annular and placed at a distance from the teeth 2f, e.g. with diameter or width larger than the teeth 2f.

The mixing group 1 then has a second component 3 with substantially tubular body and delimiting a second housing zone RZ2, such second component 3 has a third end 3a as well as a fourth end 3b. If desired, when the components of the group are in rest position and trim, the first end 2a of the first component 2 is, during use, mounted around or surrounds the third end 3a of the second component 3. The second component 3 can be extended around an axis of symmetry, during use corresponding with the axis x-x, e.g. it can comprise a solid of revolution around the axis of symmetry x-x.

The second component is also set to contain a second compound to be mixed or a vial for containing a second compound to be mixed.

In the group 1, a vial 4 can therefore be provided, if desired made of glass or similar material, which is intended to contain a second compound to be mixed; such vial 4 is arranged within the second housing zone RZ2 of the second component 3.

In the group 1, breaking or opening means 5, 6 for the vial 4 can then be provided, which protrude in the second component 3.

The breaking means can for example comprise a button element 5 intended to press the vial 4, e.g. at its tip 4a, towards the third end 3a.

The button element 5 is slidably mounted in the fourth end 3b of the second component 3 or better yet in a closure component 16 mounted, e.g. connected, if desired with snap engagement, via screwing or other engagement means, within the fourth end 3b thereof.

The breaking means can then comprise a tip or knife element 6 projecting from a base of the second component 3 at the third end 3a thereof and intended to engage the vial 4, if desired the bottom 4b thereof, when this is pressed by means of the button element 5, so as to cause the breaking of the vial 4 itself.

If desired, an elastic means or spring 11 can also be provided, for example extended in the second housing zone RZ2, e.g. starting from the internal surface of the hollow bottom wall of the second component 3, and intended to maintain the vial 4 pliably and elastically pressed towards or against the button element 5.

With regard to the vial 4, this for example can comprise a main cylindrical body having a tip on one side, if desired substantially frustoconical, and a bottom 4b on the other side, for example slightly curved with concavity directed towards the exterior of the vial 4 itself and hence, if provided, towards the tip element 6.

In addition, the first housing zone RZ1 is in fluid communication with the second housing zone RZ2, so as to allow the passage of the second compound (liquid) from the second housing zone RZ2 (or better yet from the vial 4 contained in the second housing zone RZ2) to the first housing zone RZ1, if desired with interposition of a lung zone LZ. Advantageously, the second compound cannot go backward from the first RZ1 to the second RZ2 housing zone, due to the arrangement of a suitable filter 7 for intercepting the passage opening or light 3g delimited by the third end 3a of the second component 3.

According to the embodiment illustrated in the figures and, more particularly, in FIG. 6, the filter 7 comprises a bushing element 7a delimiting a through opening intercepted by a filtering component 7b, e.g. configured as a mesh connected perimetrically to the internal face of the bushing element 7a. Such filter 7 is placed or inserted, for example to size, in the second end 3a.

In addition, the second component 3 can delimit, at the third end 3a, a seat PS for positioning the filter 7, for example via insertion, e.g. to size, of the filter 7. For such purpose, the third component can have a terminal wall 3h for closing or delimiting the second housing zone RZ2 together with a lateral wall, if desired cylindrical, 3m of the second component 3 itself. The third end 3a is then extended slightly beyond the terminal wall 3h, such that the positioning seat PS has a base or bottom delimited by the terminal wall 3h and a section of lateral casing constituted by the third end 3a. The terminal wall 3h, if provided, can delimit a plurality of through holes TH extended between the second housing zone RZ2 and the exterior of the second component 3, during use leading to the filtering component 7b.

The mixing group according to the present invention then comprises at least one third component or piston 8, it too with substantially tubular body and delimiting a second channel AC2, which is a through channel. The third component or piston 8 if desired is extended around an axis of symmetry, during use corresponding to the axis x-x, for example it can comprise a solid of revolution around an axis of symmetry x-x. In the second channel AC2 of the third component or piston 8, a lung zone LZ can be delimited, during use together with the third end 3a of the second component 3, such lung zone LZ having variable volume.

If desired, the substantially tubular body of the third component or piston 8 is at least partially mounted around the second component 3 and has an external end or fifth end 8a as well as an internal end or sixth end 8b defining a passage opening 8c, during use substantially aligned with the passage opening 3g of the second component 3 and substantially free so as to allow and not obstruct the passage of the second compound from the second housing zone RZ2 to the first housing zone RZ1.

For such purpose, the third component 8 can comprise a substantially cylindrical wall 8d on one side defining the external end 8a and on the other supporting an annular wall 8e defining the internal end 8b and delimiting the passage opening 8c.

The first housing zone RZ1 is instead the zone delimited between the internal walls of the first component 2 of delimitation of the first channel AC1, and the internal end 8b of the third component 8.

The third component 8 can be arranged between the first end 2a of the first component 2 and the third end 3a of the second component 3, i.e. the third component 8 can enclose (with sliding engagement) the third end 3a of the second component 3 and be partially enclosed (with sliding engagement) by the first end 2a of the first component 2.

In addition, the first component 2 and the third component 8 are slidable with respect to each other, while the second component 3 and the third component 8 are slidable with respect to each other. Advantageously, the relative sliding between the components 2 and 8 as well as 3 and 8 is provided along or substantially parallel to the axis of symmetry x-x.

The axis x-x actually constitutes the axis of longitudinal symmetry of the components of the group, more particularly of the components 2, 3 and 8 and of the gaskets 9 and 10.

For such purpose, the third component or piston 8 or better yet its internal end 8b is structured in a manner such to have external diameter or section substantially corresponding to or slightly smaller than the first channel AC1 delimited by the first component 2, so as to slide within and close to the delimitation walls, or better yet within and close to the substantially cylindrical 2e delimiting the latter, while the second component 3 or better yet its third end 3a is structured in a manner such to have external diameter or section substantially corresponding to or slightly smaller than the second channel AC2 delimited by the third component 8, so as to slide within and close to the delimitation walls, or better yet within and close to the substantially cylindrical wall 8d delimiting the third component 8.

The relative sliding or movement between the third component 8 and one from among the first 2 or second 3 component actually allows varying the first housing zone RZ1 or the lung zone LZ and hence obtaining a direct variation of the housing zone RZ1 or of the zones (LZ) inner to the group 1 in fluid communication with the housing zone RZ1.

Advantageously, according to the embodiment illustrated in the FIGS. 1 to 11, the volume of the first housing zone RZ1 is variable following the relative movement of the first component 2 with respect to the third component 8, with the third component 8 being integral with the second component 3, i.e. if the third component 8 is moved, the second component 3 is moved therewith and if the third component 8 is maintained stopped, also the second component 3 is maintained stopped, so as to maintain the third end 3a substantially close to and at the internal end 8a.

In addition, preferably, the volume of the lung zone LZ is variable following the relative movement of the second component 3 and the third component 8, if desired maintaining the first component 2 stopped.

For such purpose, according to the embodiment illustrated in the FIGS. 1 to 11, by moving the second 3 and the third 8 component with respect to each other, between a first rest position (see FIG. 7) and a second work position (see FIG. 8), it is possible to increase the free volume of the lung zone LZ in fluid communication with the first housing zone RZ1. This is obtainable by causing, even manually, the relative sliding of the second component 3 and of the third component 8, so as to bring the third end 3a towards the external end 8a of the third component 8, i.e., so as to extract the second component 3 from the second channel AC1. According to the embodiment illustrated in the figures, in the first rest position (see FIG. 6), the third end 3a is proximal or abuts against the annular wall 8e, while in the second work position (see FIG. 8), the third end 3a is distal from the annular wall 8e.

Still according to the embodiment illustrated in the FIGS. 1 to 11, the first 2 and the third 8 component are instead movable with respect to each other, between a first rest trim (see FIG. 10) and at least one second work trim (see FIG. 11), so as to reduce the first housing zone RZ1, thus causing, as will be better explained hereinbelow, the exit of the mixture from the first housing zone RZ1, for example through the hole 2c. This is obtainable by causing the sliding of the third component 8 together with the second component 3 or the sliding of the first component 2, so as to bring the internal end 8b towards the second end 2b and away from the first end 2a or in any case by inserting the third component 8 in the first channel AC1 so as to bring it close to the second end 2b, until it engages and pushes the mixture out from the first housing zone RZ1.

Sealing means 9, 10 are then provided between the first component 2 and the third component 8 as well as between the second component 3 and the third component 8.

Advantageously, the sealing means comprise at least one first gasket 9, if desired annular, which is arranged between the first component 2 and the third component 8, so as to ensure the seal, in particular of the first housing zone RZ1, between first 2 and third 8 component, as well as at least one second gasket 10, if desired annular, between the second 3 and third component 8, so as to ensure the seal, in particular of the first housing zone RZ1 or, if provided, also of the lung zone LZ, between the second 3 and third 8 component.

More particularly, the sealing means are set for ensuring the sealing connection between the respective components, hence the first gasket 9 between the first component 2 and the third component 8, and the second gasket 10 between the second component 3 and the third component 8.

Still more particularly, the sealing means are set for ensuring the seal, and hence the entrance or exit of fluids, in particular including air, into the or from the internal zones of the group, which comprise the first housing zone RZ1, the second housing zone RZ2, along with, if provided, the lung zone LZ. Therefore, the first housing zone RZ1 is in sealing fluid communication with the second housing zone RZ2, if desired with interposition of the lung zone LZ.

For such purpose, the components 2, 3 and 8 of the group are made of a fluid seal material, if desired a plastic or composite material, so as to prevent the passage of the fluid (in particular air and liquid or second compound) through the walls thereof, and to allow such passage only through holes or openings provided at the ends 2a, 2b, 3a, 3b, 8a, 8b thereof, except for the closure of the same by means of suitable components that will be mentioned hereinbelow, or through outlets set for being placed in fluid communication with suitable pressurized fluid suction means.

The first gasket 9 has hardness or strength different from, i.e. greater or lesser than, the second gasket 10, hence preferably the gaskets 9 and 10 do not have equal hardness or strength. More particularly, the hardness of the first gasket can be, merely by way of a non-limiting example, between 70 and 150 Shore degrees, while the hardness of the second gasket can be, merely by way of a non-limiting example, between 50 and 70 Shore degrees.

However, in addition to the hardness of the gaskets, also the coupling interference of the components with the gaskets is of importance.

In addition, alternatively both gaskets 9 and 10 could have the same hardness, but the coupling of the first gasket 9 with the first component 2 and with the third component 8 has a stability or strength different from the coupling of the second gasket 10 with the second component 3 and with the third component 8, such that the seal between second component 3 and third component 8 is different from the seal between first component 2 and third component 8.

More particularly, there could be a gasket (e.g. the first gasket 9) with very precise coupling within the respective housing or with the respective components (e.g. the components 2 and 8) and which leads to a high hardness of maneuvering between such components (2 and 8), while the other gasket (e.g. the second gasket 10) can have a loose coupling within the respective housing or with the respective components (e.g. the components 3 and 8), and this would induce a relative ease of maneuvering between such components (3 and 8).

According to the embodiment described above, the first gasket 9 can have a hardness much greater than the second gasket 10.

The first gasket 9 (as a function of its hardness or of the strength of the coupling with the components 2 and 8) carries out the function of hydraulic seal between first component 2 and third component 8 and can also ensure the maintenance in position of the same components when the second component 3 is moved with respect to the third component 8 (see FIGS. 7 and 8).

The first gasket 9 can be an annular gasket housed in a slot or the like delimited between an external section of the third component 8 and an internal section of the first component 2. According to the embodiment illustrated in the figures, the internal end 8b of the third component 8 is substantially flanged, i.e. the annular wall 8e has external diameter or width greater than the substantially cylindrical wall 8d and then provides for a ring element 8f extended from an external section of the third component 8 close to the flanged internal end 8b, but at a distance from the same, so as to delimit a recess 8g therewith, if desired annular, open outward and during use externally closed by the first component 2.

With regard instead to the annular second gasket 10, this can be fit on the third end 3a of the second component 3 and comprises a main cylindrical section 10a with one end proximal to the third end 3a and one end distal from the third end 3a, and (the second gasket 10) also comprises a first annular section 10b protruding from the proximal end of the main cylindrical section 10a towards the interior of the group or, during use, towards the axis of symmetry x-x thereof, so as wrap around the third end 3a of the second component 3.

If desired, the second gasket 10 also comprises a second section 10c, e.g. annular, protruding from the distal end of the main cylindrical section 10a within an annular recess 3d delimited by the second component 3 at the third end 3a thereof.

In such case, in the first rest position, the first annular section 10b of the second gasket 10 is comprised between the third end 3a and the annular wall 8e.

The second gasket 10 can then be provided with ribs 10d protruding, for example, towards the exterior of the gasket, if desired from the main section 10a or from the first annular section 10b and set for increasing the seal between the components 3 and 8.

According to the embodiment illustrated in the figures, the second gasket 10 delimits an opening 10f substantially aligned with the positioning seat PS and with the filtering component 7b.

The mixing group 1 can then be provided with an abutment component, e.g. sleeve-shaped 12, fit on the first end 2a and intended to prevent the removal of the third component 8 or better yet of the internal end 8b thereof from the first channel AC1 delimited by the first component 2.

More particularly, the sleeve-shaped component 12 can have annular or tubular configuration with a section 12a projecting internally with respect to the first component 2 and having internal diameter or section smaller than the internal end 8b of the tubular component 8, so as to delimit a first shoulder 12b intended to be abutted (with components 2 and 8 arranged in the first rest trim) against the internal end 8b of the latter or a projecting section thereof at the latter, e.g. the ring element 8f.

The sleeve-shaped element 12 can be engaged with the first end 2a of the first component 2, via bayonet-coupling, via screwing or via forced insertion. According to the embodiment illustrated in the figures, the sleeve-shaped element 12 has substantially L-shaped seats 12c via insertion or bayonet engagement of the teeth 2f.

The first 2 and the third 8 component are movable, as stated above, with respect to each other, between a first rest trim (see FIGS. 9 and 10), in which the internal end 8b is proximal to the first end 2a of the first component 2, if desired with the ring element 8f in abutment against the first shoulder 12b, and a second work trim (see FIG. 11), in which the internal end 8b is distal from the first end 2a and proximal to the second end 2b. According to the embodiment illustrated in FIGS. 1 to 11, in the passage of the first 2 and third 8 component from the first to the second trim, the first housing zone RZ1 is reduced, thus causing, as will be better explained hereinbelow, the exit of the mixture from the first component 2, e.g. through the hole 2*c*.

In addition, the mixing group can also have components 13*a*, 13*b* connecting the third component 8 to the second component 3, more particularly the external end 8*a* of the third component 8 to an external intermediate portion of the second component 3.

Figure 2:
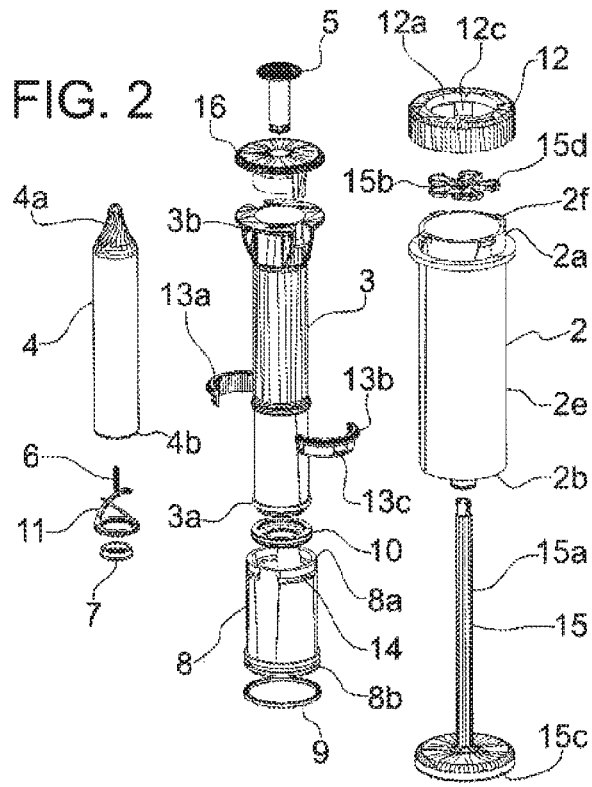
FIGS. 2 and 3 are exploded views of the group of FIG. 1.
Figure 3:
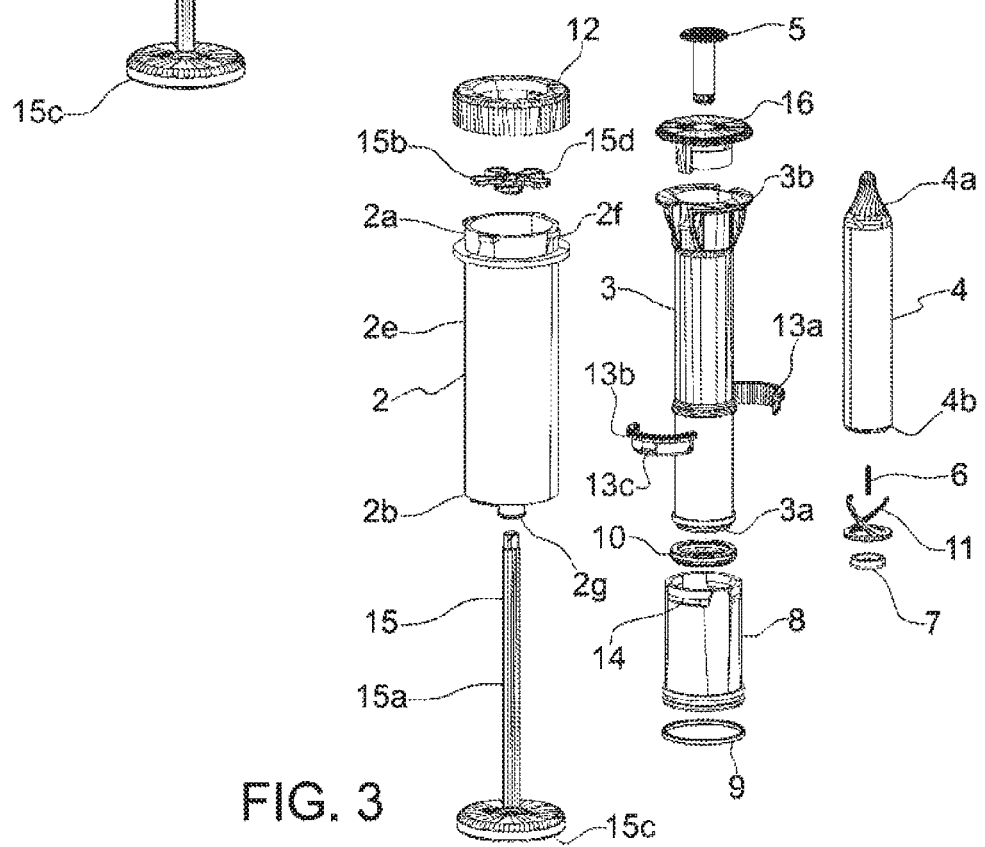
Figure 4:
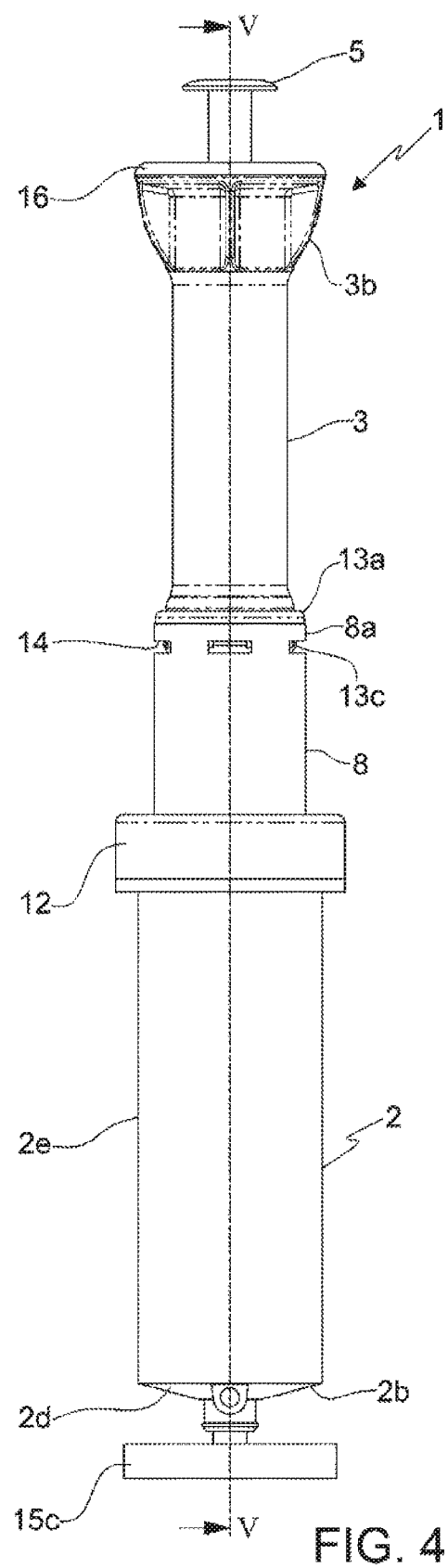
FIG. 4 is a side view of the group of FIG. 1.
Figure 5:
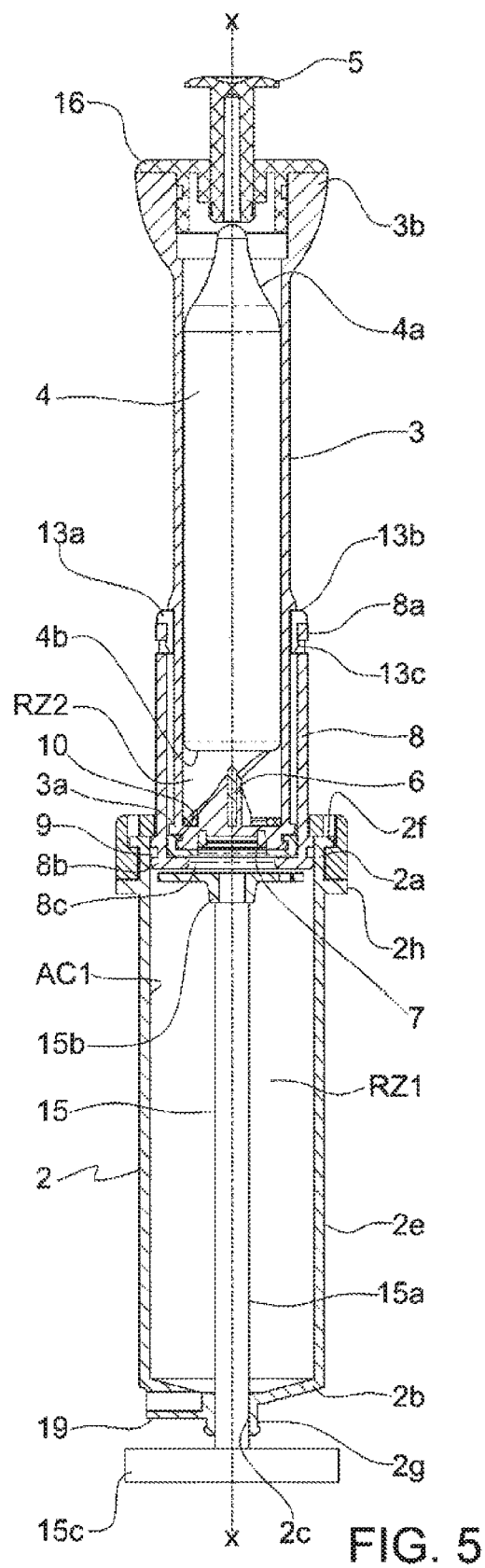
FIG. 5 is a sectional view taken along the line V-V of FIG. 4.

More particularly, the connector components can comprise two half-rings 13*a*, 13*b* mounted around the second component 3 and brought into abutment against each other at respective ends; such half-rings 13*a*, 13*b* have one or more projections 13*c* intended to engage, e.g. snap engage, respective grooves 14, if desired through grooves, formed in the external end 8*a* of the third component 8 (see in particular FIGS. 2 to 4).

The mixing group can then comprise a mixing unit 15 within the first housing zone RZ1, which is set to operate in such zone RZ1 so as to mix the first and the second compound. If desired, the mixing unit 15 is provided with a stem 15*a*, e.g. slidably mounted in the hole 2*c*, a mixing rotor or impeller 15*b* supported at a first end of the stem 15*a* and intended to be rotated, by means of rotation of the stem 15*a*, within the first housing zone RZ1. The mixing unit 15 then comprises a handle 15*c* connected, if desired fixed, to the other end of the stem 15*a* and during use arranged outside the first housing zone RZ1, by means of which it is possible to drive the rotation of the mixing rotor 15*b*.

The stem 15*a* and the mixing rotor 15*b* can be constrained by means of removable engagement means, e.g. by means of bayonet engagement or screwing.

Alternatively, the stem 15*a* can be broken or in any case released from the mixing rotor 15*b*, e.g. making the same in two parts that are connected to each other by means of removable engagement means, e.g. bayonet, screw or similar means.

In addition, the mixing rotor 15*b* centrally delimits a fourth through channel AC4. For such purpose, if a mixing unit 15 is provided as illustrated in the figures, once the stem 15*a*, as will also be discussed hereinbelow, has been removed from the hole 2*c* and freed from the mixing rotor 15*b*, the mixture obtained with the group can be thrust outside the group (in particular outside the second gasket 10 and the filtering component 7*b*) itself, by making it pass through the fourth channel AC4 substantially aligned with or within the hole 2*c*.

Advantageously, the mixing rotor 15*b* delimits passage windows, for example it can have a plurality of blades 15*d* or the like delimiting passage windows therebetween intended to allow the passage of the second compound and the entrance thereof into the first housing zone RZ1.

Alternatively, the mixing unit 15 can be structured differently, or it can be arranged that at the time of extraction and breakage or release of the stem 15*a*, the components of the mixing unit 15 that remain within the group do not obstruct the outlet hole or opening for the mixture. According to a variant that is less preferred, the mixing unit 15 could also comprise a mass mounted in the first housing zone RZ1 and free to slide within the same.

In addition, a mixing group according to the present invention, if desired the first component 2, can be provided with at least one filler 19, for example at or leading to the first housing zone RZ1, which is set for being placed in fluid communication with suction means, which allow applying a good suction of the liquid from the second housing zone RZ2 to the first housing zone RZ1 and/or the suction of air from the first housing zone RZ1 during the mixing of the compounds, as will be clearer hereinbelow.

Such suction means, which generate a reduction of pressure within the first housing zone RZ1, can also or only be driven during the mixing of the first and the second compound, in order to reduce the formation of bubbles of the mixture and improve the properties thereof.

For such purpose, the movements of the stem 15*a* of the mixing unit 15 can cause air leaks at the hole 2*c*, with consequent load losses, which are balanced due to the suction means.

The suction means can comprise, for example, devices driven by means of electric motor or according to Venturi effect. Alternatively, the group can be placed in fluid communication with a centralized vacuum line provided, for example, in the operating rooms.

In one version of the invention, such mixture is a bone cement for medical uses.

In the absence of the connection with the suction means, the outlet could then be sealingly closed by means of suitable cover.

In addition, in the filler 19, a filter baffle (not illustrated in the figures) could be inserted which has the function of allowing the passage of air, while retaining powder; however the filler 19 is not placed in fluid communication with the suction means. In such case, the suction means could be placed in fluid communication with a though hole or opening, if desired at the second housing zone RZ2, e.g. provided in the second component 3 or in the button element.

For such purpose, the button element could be structured as illustrated in FIGS. 12 to 15.

More particularly, the button element 50 delimits a through hole 50*a*, in which the following are housed in hermetic conditions: a filter baffle 50*b*, intended to block the passage of the second compound (liquid) while allowing the passage of air, as well as a check valve 50*c*. Still more particularly, in the through hole 50*a*, from the exterior towards the interior of the group or better yet closer to the first end 2*b*, first the check valve 50*c* and then, substantially in series, the filter baffle 50*b* are housed. The check valve 50*c*, along with the filter baffle 50*b*, are inserted substantially to size, at least for part of their longitudinal extension or along the axis of symmetry x-x, in a respective section of the through hole 50*a*, such that each of these intersects or substantially entirely occupies a respective longitudinal section of the through hole 50*a*.

Clearly, a group according to the present invention could also be provided with suction means sealingly connected or connectable to one of the above-indicated outlets.

The mixing group could then be provided with a bellows component or the like mounted around the button element 5, 50 and intended to allow an action of pumping the second compound, so as to facilitate the transfer thereof from the second RZ2 to the first RZ1 housing zone.

Figure 16:
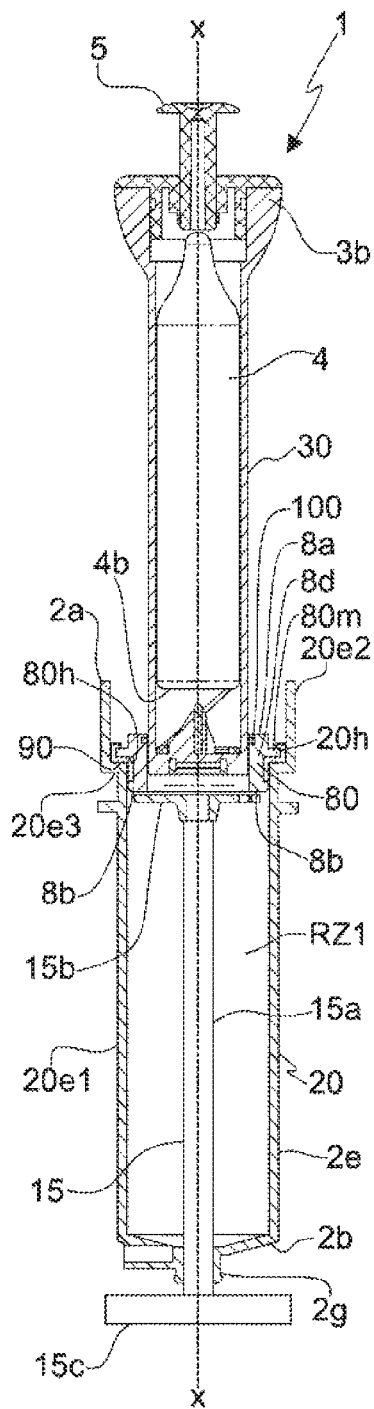
FIGS. 16 to 18 are views similar to FIG. 5 of other embodiments of the mixing group according to the present invention.

According to a variant illustrated in FIG. 16, the first component 20 delimits at least one second shoulder 20*h* directed towards the fourth end 3*b*, and the first 20 and the third 80 component are movable with respect to each other between a third position or trim, in which the second shoulder 20*h* is proximal and in abutment, if desired with interposition of a first gasket 90, against the internal end 80*b* or a third shoulder 80*h* of the third component 80, and a fourth position or trim (not illustrated in figure) in which the second shoulder 20*h* is distal from the internal end 80*b* or from the third shoulder 80*h*.

In such case, the first component 20 can comprise a first segment 20*e*1 corresponding to the substantially cylindrical section 2*e* mentioned above as well as a second segment 20*e*2, distal from the second end 20*b* with respect to the first segment 20e1 and with external diameter or width greater than the first segment 20e1 and connected to the latter by means of an annular section 20e3 delimiting the second shoulder 20h.

In addition, the third component 80 can comprise a substantially cylindrical wall 8d on one side defining the external end 8a and on the other side defining the internal end 8b, the third component 80 then comprising an annular segment 80m protruding from the exterior of an intermediate portion of the substantially cylindrical wall 8d; such intermediate portion is placed between the external end 8a and the internal end 8b. In such case, the third shoulder 80h is delimited by the annular segment 80m.

According to such variant, the second gasket 100 is housed in a slot or the like delimited between an internal section of the third component 80 and an external section of the second component 30, while the first gasket 90 is connected to the second shoulder 20h or to the third shoulder 80h or mounted on one of these.

Figure 12:
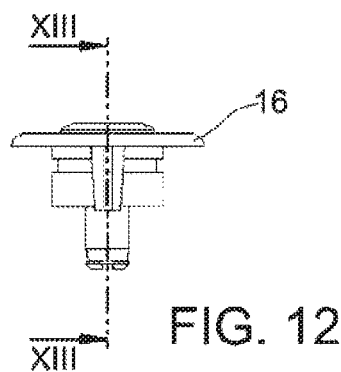
FIG. 12 is a side view of a variant of a detail of a group according to the present invention.
Figure 17:
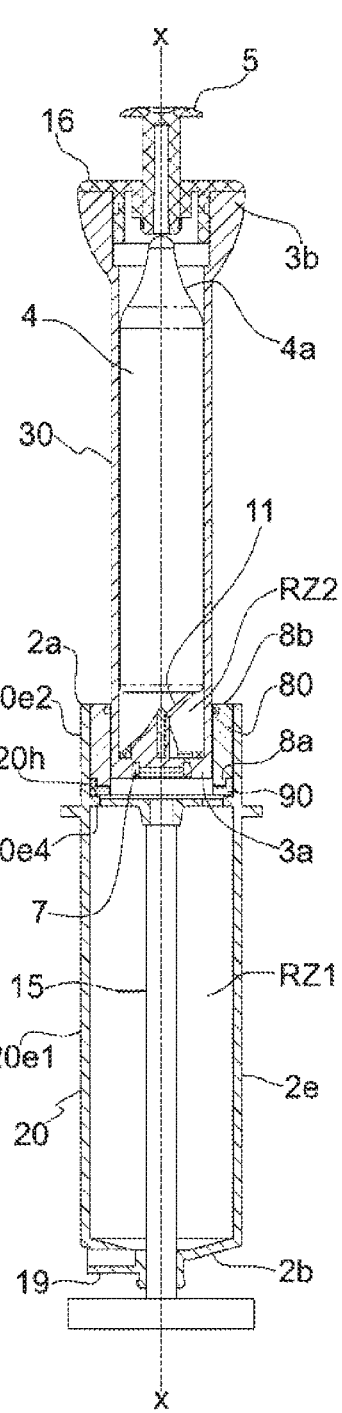

The embodiment illustrated in FIG. 17 is very similar to that of FIG. 12, but the first component 20 comprises an annular section 20e4 delimiting the second shoulder 20h and protruding towards the interior starting from an intermediate portion of the substantially cylindrical section, so as to divide it into a first segment 20e1 and a second segment 20e2 that are substantially aligned and with equal external and internal diameter and bulk.

The third component 80, however, is substantially straight, hence lacking projecting parts, such that the first 20 and the third 80 component are movable with respect to each other between a rest position, in which the second shoulder 20h is proximal and in abutment against the internal end 8b of the third component 80, and a fourth work position in which the second shoulder 20h is distal from the internal end 8b. In such case, the first gasket 90 is connected to the internal end 8b or to the annular section 20e4 or mounted on one of these.

Figure 13:
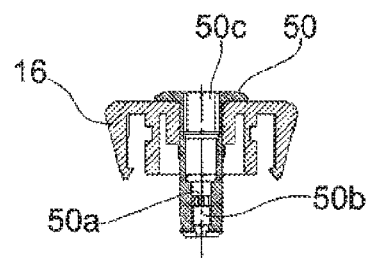
FIG. 13 is a sectional view along the line XIII-XIII of FIG. 12.
Figure 14:
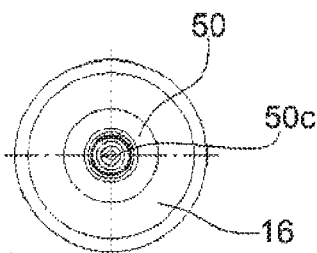
FIG. 14 is a plan view of the detail of FIG. 12.
Figure 15:
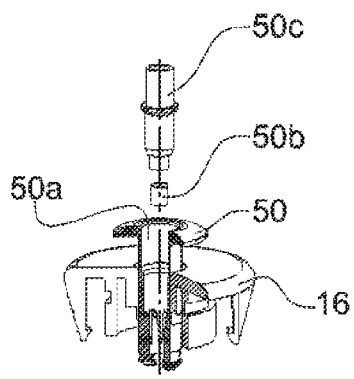
FIG. 15 is an exploded and sectional view of the detail of FIG. 12.
Figure 18:
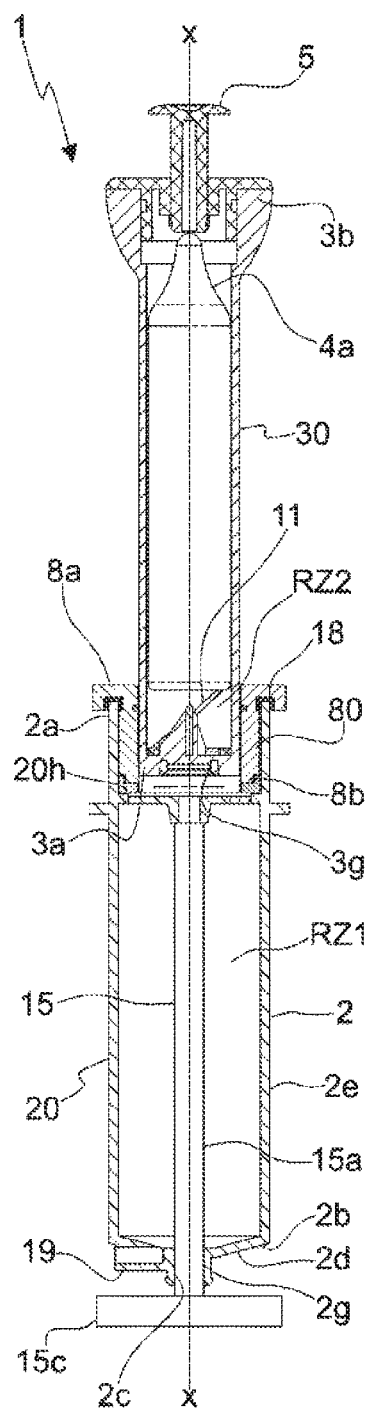

With reference now to FIG. 18, an embodiment of a mixing group according to the present invention is illustrated which substantially corresponds to the embodiment of FIG. 13, but in which the third component 80 has external end 8a bent substantially as a U or C, so as to delimit a reception and abutment cradle of the free end of the first component 2, when the latter is in the rest position.

In such case, the group can also be provided with a third gasket 18, if desired annular, for example U or C shaped, which is connected/mounted to/on the free end of the first component 2 or in the external end 8a.

In accordance with the embodiments of FIGS. 16 to 18, the volume of the first housing zone RZ1 is variable following the relative movement of the second component 30 with respect to the third component 80, with the first component 20 integral with the third component 80, i.e., if the third component 80 is moved, the first component 20 is moved therewith and if the third component 80 is maintained stopped, also the first component 20 is maintained stopped.

In accordance with the embodiments described with reference to FIGS. 16 to 18, the first gasket 90 can have a hardness much less than the second gasket 100, or the first gasket 90 has a coupling with the first component 20 and with the third component 80 with stability or strength that is different from the coupling of the second gasket 100 with the second component 30 and with the third component 80.

In such case, the second gasket 100 (as a function of its hardness or of the strength of the coupling with the components 30 and 80) carries out the function of hydraulic seal between second component 30 and third component 80 and can also ensure the maintenance in position of the same components when (as will be clearer hereinbelow) the first component 20 is moved with respect to the third component 80.

A group according to the present invention could also be structured so as to combine the embodiment illustrated in the FIGS. 1 to 11 with one of the embodiments of FIGS. 16 to 18, and in such case one could for example have the second and the third component substantially like those of the embodiment of FIGS. 1 to 15 and a first component similar to that of FIGS. 16 to 18; in such case, after having connected the first component and the second component and, if a vial is provided, after having broken the vial, one could move the third component with respect to the second so as to increase the lung zone LZ and move the third component with respect to the first so as to increase the first housing zone RZ1.

Figure 19:
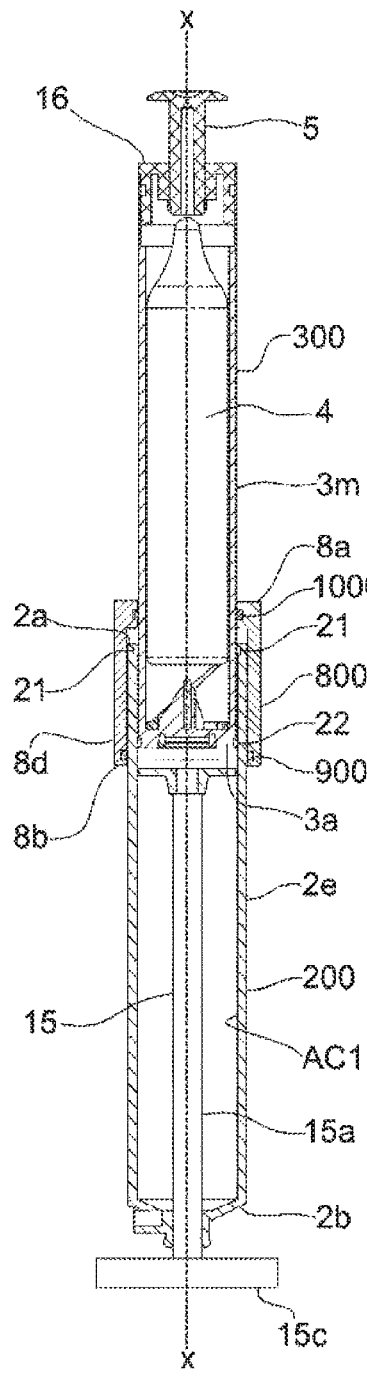
FIGS. 19 to 21 are views of a mixing group according to the present invention in accordance with another embodiment in respective operating steps.
Figure 20:
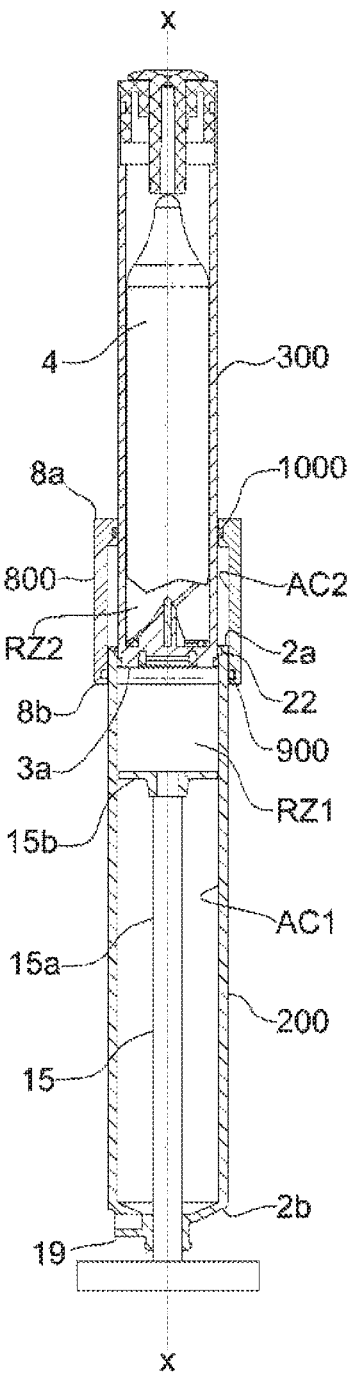
Figure 21:
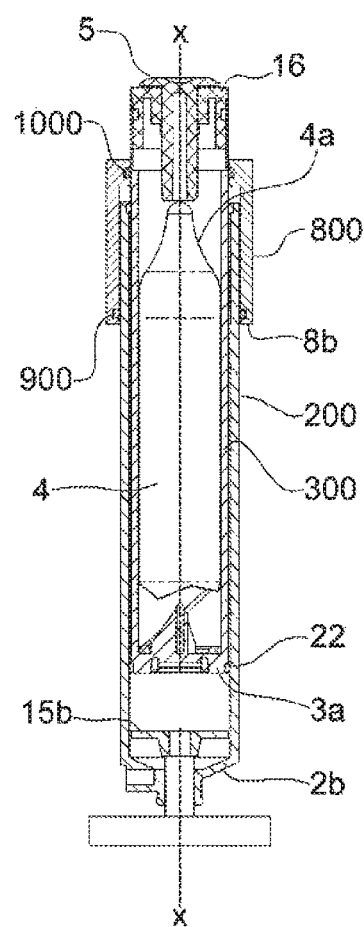

In accordance with a further variant illustrated in FIGS. 19 to 21, the third component 800 is outside the first 200 and second 300 component and, more particularly, it surrounds the first end 2a and the third end 3a as well as part of the first component 200 and the second component 300.

In such case, both the ends 8a and 8b of the third component 800 are external and more particularly the fifth end 8a is external and encloses a section of the second component 300, while the sixth end 8b is external and encloses a section of the first component 200. For such purpose, the third component 800 is substantially tubular, if desired with fifth end 8a with ribs or protuberances, for example annular, protruding towards the interior or towards the axis x-x and delimiting, between them and an external section of the second component 300, a seat for the second gasket 1000.

In such case, the second component 300 or better yet its third end 3a is structured in a manner such to have external diameter or section substantially corresponding to or slightly smaller than the first channel AC1 delimited by the first component 200, so as to slide within and close to the delimitation walls, or better yet within and close to the substantially cylindrical section 2e delimiting such component. In addition, the first component 200 or better yet a section thereof at its first end 2a is structured in a manner such to have external diameter or section substantially corresponding to or slightly smaller than the second channel AC2 delimited by the third component 800, so as to slide within and close to the delimitation walls, or better yet within and close to the substantially cylindrical wall 8d delimiting such component.

The first gasket 900 can instead be housed in a slot or the like delimited between an external section of the first component 200 and an internal section of the third component 800, in particular at the sixth end 8b.

The group can then comprise gasket means between the first 200 and the second 300 component. The gasket means can comprise a fourth gasket 21 and/or a fifth gasket 22, if desired annular, each housed in a slot or the like delimited between an external section of the second component 300 and an internal section of the first component 200, in particular at the third end 3a (fifth gasket 22) or at the first end 2a (fourth gasket 21).

In accordance with the embodiment illustrated in FIGS. 19 to 21, the first gasket 900 can have a hardness much less than the second gasket 1000, or the first gasket 900 has a coupling with the first component 200 and with the third component 800 with stability or strength different from (if desired less than) the coupling of the second gasket 1000 with the second component 300 and with the third component 800. The fourth 21 and fifth 22 gasket can have hardness or coupling with the respective components less than the second gasket 1000 and substantially equal to the first gasket 900.

In addition, a group according to the embodiments of FIGS. 16 to 21 could also be provided with abutment or connector components similar to or with similar function to the abutment or connector components illustrated with reference to the embodiment of FIGS. 1 to 11.

Figure 22:
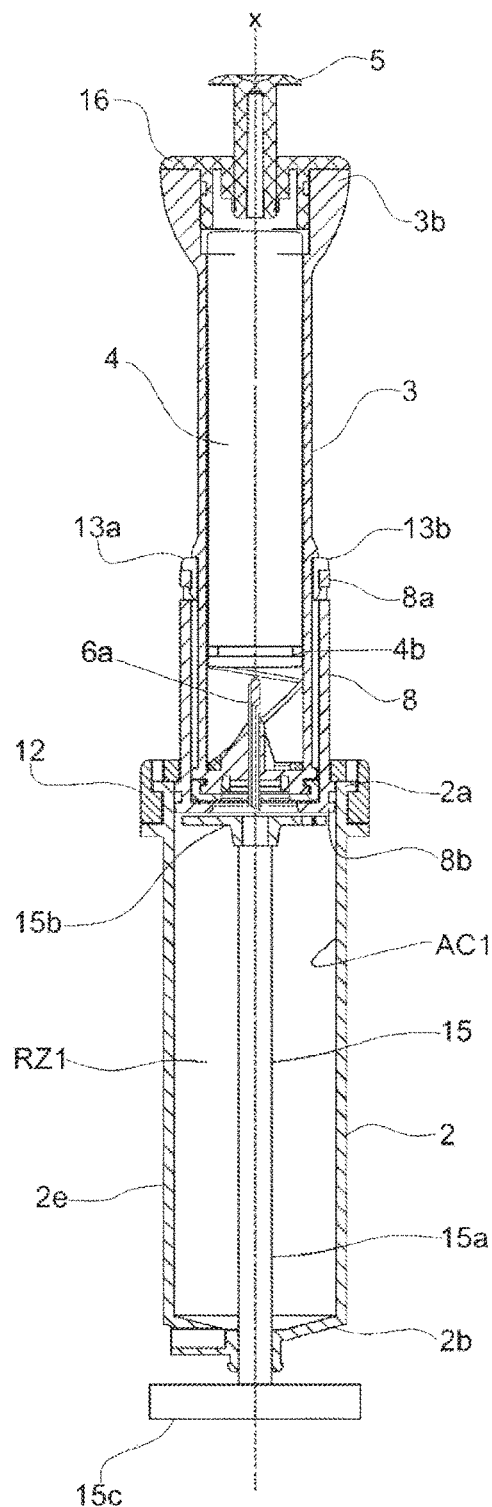
FIG. 22 is a view of a mixing group according to the present invention in accordance with another embodiment.
Figure 23:
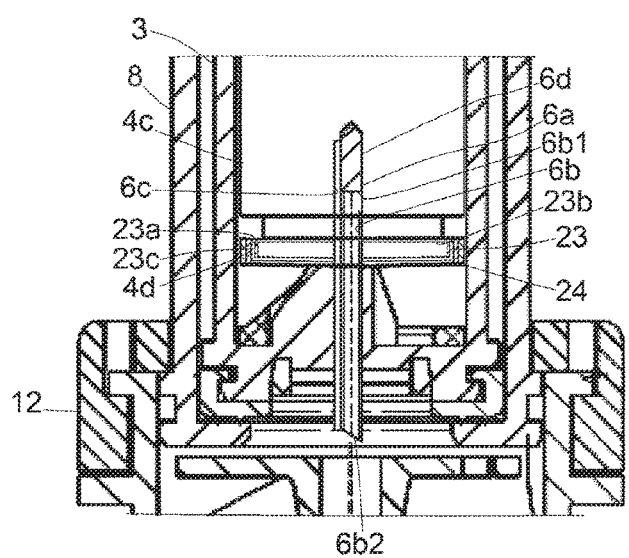
FIG. 23 is a view of an enlarged scale detail of the mixing group of FIG. 22 in vial open position.

With reference now to the embodiment illustrated in the FIGS. 22 and 23, this is very similar to the embodiment of FIG. 1, but the group comprises a vial 4 with a containment body 4c, e.g. made of glass, delimiting an (open) end 4d at which a cap component 23 is mounted, mounted to close the end 4d, so as to ensure the sealing of the vial 4 and prevent the undesired exit of the second compound therefrom; for such purpose, the cap component 23 or a film thereof is impermeable to the second compound.

The cap component 23 is for example fixable in position on the containment body 4c by means of a ring nut 24 or the like, e.g. made of aluminum, which can be annular. The cap component 23 or better yet a part thereof can be perforable; for such purpose the cap component 23 can have a support body 23a, e.g. annular, and on an internal side, internal during use (inside the vial 4), thereof a film 23b is fixed that is impermeable to the second compound and perforable by means of breaking or opening means for the vial 4. If desired, outside the support body 23a, the cap component 23 can have a mesh component 23c or the like wound on the support body 23a.

The breaking or opening means can instead a comprise a needle or perforator 6a of the cap component 23 or of a part thereof set to allow the conveyance or flow of the second compound outside the vial 4 and within or towards the first housing zone RZ1, if desired upon passage through the lung zone LZ. According to the non-limiting embodiment illustrated in the figure, the needle 6a comprises a double-flow perforator, which can have a first channel 6b, e.g. substantially central, for the conveyance or flow of the second compound outside the vial 4, as well as a second channel 6c, for example with section smaller than the first channel 6b, for the passage of air into the vial 4, in particular when the second compound exits from the same.

More particularly, the first channel 6b can have an inlet opening 6b1, during use proximal to the vial 4 and distal from the first housing zone RZ1, as well as an outlet opening 6b2 leading into the first housing zone RZ1 or in any case proximal thereto with respect to the inlet opening 6b1. The second channel 6c can instead have an introduction opening distal from the vial 4 and proximal to the first housing zone RZ1 as well as an exit opening distal from the first housing zone RZ1 with respect to the introduction opening.

The perforator 6a can have a tip 6d set to open the vial 4, for example, if provided, to open or perforate a cap component 23 or a film 23b thereof, for example passing through the axial opening of the support body 23a and, if provided, of the ring nut 24, in particular when the vial 4 is pressed, e.g., by means of the button element 5.

According to the present invention, a method is also provided for mixing two compounds to obtain a mixture, which comprises the following steps:
placing a first compound, such as a powder, in a first housing zone RZ1 delimited by a first component 2, 20, 200 having a substantially tubular body,
inserting a second compound to be mixed or a vial 4 containing a second compound (such as a liquid) to be mixed in a second housing zone RZ2 delimited by a second component 3, 30, 300 with substantially tubular body,
arranging at least one third component 8, 80, 800 with substantially tubular body,
arranging sealing means 9, 10, 90, 100, 900, 1000,
connecting the first 2, 20, 200 and the second 3, 30, 300 component with interposition of the third component 8, 80 between a first end 2a of the first component 2, 20 and a third end 3a of the second component 3, 30 or with the third component 800 enclosing the first end 2a and the third end 3a, as well as with interposition of the sealing means 9, 10, 90, 100, 900, 1000 between first component 2, 20, 200 and the third component 8, 80, 800 as well as between second component 3, 30, 300 and third component 8, 80, 800, in a manner such that:
the first component 2, 20, 200 and the third component 8, 80, 800 are slidable with respect to each other, while the second component 3, 30, 300 and the third component 8, 80, 800 are slidable with respect to each other, and
the first housing zone RZ1 is in fluid communication with the second housing zone RZ2,
if a vial is provided, breaking or opening the vial within the second component 3, 30, 300,
moving the first component 20, 200 with respect to the third component 80, 800 and/or the second component 3 with respect to the third component 8, in a manner such to increase the first housing zone RZ1 and/or a lung zone LZ comprised between the first housing zone RZ1 and the third end 3a, so as to cause the passage of the second compound from the second housing zone RZ2 to the first housing zone RZ1,
mixing the first and the second compound in the first housing zone RZ1 so as to obtain a mixture, and
moving the first component 2 with respect to the third component 8 or the second component 30, 300 with respect to the third component 80, 800, in a manner such to decrease the first housing zone RZ1, so as to cause the exit of the mixture from a second end of the first component.

In order to facilitate the passage of the second compound from the second housing zone RZ2 to the first housing zone RZ1, the step of moving the first component 20, 200 with respect to the third component 80, 800 and/or the second component 3 with respect to the third component 8, in a manner such to increase the first housing zone RZ1 and/or a lung zone LZ comprised between the first housing zone RZ1 and the third end 3a, can be repeated multiple times to stimulate the operation of a plunger.

If a mixing group is used according to FIGS. 1 to 11 for achieving a method in accordance with the present invention, then after having assembled the group a first compound, such as a powder, is placed in the first housing zone RZ1, the vial 4 (see FIG. 7) or a cap component 23 thereof (see FIG. 23) is broken or opened, if desired with the breaking or opening means 5, 6 or 6a, and the second component 3 is moved, even manually, with respect to the third component 8 (see FIG. 8), in a manner such to increase the free area of the lung zone LZ, this being obtained by moving the second component 3 so as to bring the third end 3a thereof towards the external end 8a of the third component 8 or by removing the second component 3 from the second channel AC2. In such a manner, since the volume of the lung zone LZ is actually increased, the pressure inside the same is in fact reduced, thus causing the passage of the second compound from the second housing zone RZ2 to the lung zone LZ and partly into the first housing zone RZ1. In order to complete the passage of all of the second compound (liquid) from the lung zone LZ to the first housing zone RZ1, the second component 3 is moved backward, even manually, with respect to the third component 8 (see FIG. 9) in a manner such to decrease the lung zone LZ, which causes the passage of the residual liquid from the latter to the first housing zone RZ1.

In order to facilitate the passage of the second compound from the second RZ2 to the first RZ1 housing zone and/or during the mixing of the compounds, the mixing group can be placed in communication with suitable pressurized fluid suction means so as to facilitate the passage of the second compound into the first housing zone RZ1.

At this point, for example by means of the mixing unit 15, the first and the second compound are mixed in the first housing zone RZ1, until the mixture is attained. If a mixing unit 15 is provided as illustrated in the figures, for the mixing it is possible to make the mixing rotor 15b to rotate and (simultaneously) move the stem 15a and hence the mixing rotor 15b in the direction of the axis x-x, alternatively moving closer to or away from the second end 2b.

Subsequently, one moves, if desired by means of a suitable instrument such as a pneumatic gun, the third component 8, integrally with the second component 3, for example due to the action of the second gasket 10, within the first channel AC1 of the first component 2, in the direction of the second end 2b of the latter (see FIG. 10), so as to cause the exit of the mixture from the second end 2b of the first component 2, if desired from the hole 2c.

If a mixing unit 15 has been provided like that illustrated in the figures, before moving the third component 8 in the direction of the second end 2b, the stem 15a of the mixing unit 15 is removed from the first channel AC1, until the mixing rotor 15b of the same is brought to the second end 2b of the first component 2 and, if desired, the stem 15a is broken or the same is freed from the mixing rotor 15b (see FIG. 10). In such case, the mixture could be thrust outside the group upon passage through the fourth channel AC4.

If instead a method according to the present invention is implemented by using a mixing group according to FIGS. 16 to 18, after having connected the first component and the second component and if provided a vial, after having broken or opened the vial 4 or a cap component 23 thereof, the following steps are executed:

the first component 20 is moved, even manually, with respect to the third component 80, in a manner such to increase the first housing zone RZ1 and thus actually cause the passage of the second compound from the second housing zone RZ2 to the first housing zone RZ1, mixing, for example by means of the mixing unit 15, the first and the second compound in the first housing zone RZ1 so as to obtain the mixture, and the second component 30 is moved with respect to the third component 80, if desired by means of a suitable instrument, such as a pneumatic gun, and thus the second component 30 is moved close to the second end 2b, in a manner such to decrease the first housing zone RZ1, thus causing the exit of the mixture from the second end 2b of the first component 20 or better yet from the hole 2c, if desired by passing through the fourth channel AC4.

If instead a method according to the present invention is implemented by using a mixing group according to FIGS. 19 to 21, after having broken or opened vial 4 or a cap component 23 thereof, the following steps are executed:

the first component 200 is moved, even manually, with respect to the third component 800 (if desired maintaining stopped the second component 300, for example due to the action of the second gasket 1000) (see FIG. 20) in a manner such to increase the first housing zone RZ1 and thus actually cause the passage of the second compound from the second housing zone RZ2 to the first housing zone RZ1, mixing, for example by means of the mixing unit 15, the first and the second compound in the first housing zone RZ1 so as to obtain the mixture, and the second component 300 is moved with respect to the third component 800 and the second component 200 (see FIG. 21), more particularly within the first channel AC1, if desired by means of a suitable instrument, such as a pneumatic gun, and thus the second component 300 is brought close to the second end 2b, in a manner such to decrease the first housing zone RZ1, thus causing the exit of the mixture from the second end 2b of the first component 200 or better yet from the hole 2c, if desired by passing through the fourth channel AC4.

Before such step, the first component 200 can be moved backward, even manually, with respect to the third component 800.

In addition, if a button element 50a is provided for as well as, if desired, a filter baffle 50b and a check valve 50c, after the button element 50 has been pressed in order to break or open the vial 4 and the components 3 and 8 or 20, 200 and 80, 800 have been moved in a relative manner, so as to cause the passage of the second compound (liquid) into the first compound (powder), a tube is connected, in fluid communication with the suction means, with the through hole 50a and the suction means are driven so as to place the group or better yet the respective housing zones "under vacuum" or in any case under depression. Subsequently, the group is disconnected from the suction means or the action thereof is interrupted, but in any case, due to the presence, if provided, of the check valve 50c, the depression is maintained. At this point, the compounds are mixed, as stated above, until the mixture is obtained.

In such case, therefore, the depression or suction could be achieved only during the mixing and not for facilitating the descent of the liquid from the second RZ2 to the first RZ1 housing zone. In order to make the second compound or liquid to pass from the second RZ2 to the first RZ1 housing zone, the first component 20, 200 in such case could be repeatedly moved, like a plunger, with respect to the third component 80, 800 and/or the second component 3 could be repeatedly moved, like a plunger, with respect to the third component 8.

Alternatively, suction could first occur at the filler 19 in order to facilitate the descent of the liquid, and then at the hole 50a as stated above.

As will be understood, a group according to the present invention is simple and easy to use and ensures a good seal, in particular of the first housing zone RZ1, due to the presence of the third component 8, 80, 800 along with the sealing means 9, 10, 90, 100, 900, 1000, in particular with two gaskets, one harder 9, 100, 1000 or stronger and the other 10, 90, 900 less hard or weaker or in any case with coupling having different stability or strength.

Due to one such group, in fact, unlike the groups according to the state of the art, it is possible to differentiate the components involved in the movements to be imparted to the components, i.e. by completing a first step of increase of the first housing zone RZ1 or of a third zone LZ communicating with the latter, moving two components of the group in a relative manner (the second 3 and the third 8 according to the variant of FIG. 1-11, if desired maintaining stopped the first 2, and the first 20, 200 and the third 80, 800 according to the variants of FIGS. 16-21, if desired maintaining stopped the second 30, 300, or the second 3 and the third 8 as well as the first 20 and the third 8, according to the combination of the provided embodiments), while the subsequent second step of thrusting the bone cement outside the group is obtained with a relative movement of another two components (the third 8 (integral with the second 3) with respect to the first 2 according to the variant of FIG. 1-11 and the third 80, 800 (integral with the first 20, 200) with respect to the second 30, 300 in accordance with the variants of FIGS. 16-21).

In addition, providing for sealing means, comprising two gaskets with different hardness or strength or with different coupling with respective components of the group, allows, during the first step, actuating a relative movement of the components between which the softer gasket is placed, such step being manually completable, whereas during the second step, usually conducted with a suitable instrument, allows the relative movement of the components between which the harder gasket is placed.

For such purpose, in particular with reference to the embodiments of FIGS. 1 to 11, the softer gasket, less strong or with weaker coupling with the respective components, the only gasket at which the external air can pass, is far from the first housing zone RZ1; also considering the specific structure of the third component 8, such gasket does not compromise the mixture formation step.

This is in any case also ensured with the other illustrated embodiments, in particular that of FIGS. 17 to 21.

In addition, in a group according to the present invention, it is possible to provide for a soft gasket or in any case one with weaker coupling and with the respective components of the group, with size (section) much reduced with respect to the gaskets provided in the groups according to the state of the art, and also due to such expedient the manual movement is facilitated (during the first step in which the volume of the first housing zone is increased) between the components of the group.

Modifications and variants of the invention are possible within the protective scope defined by the claims.

Thus, for example, a mixing group according to the present invention might not comprise a vial and means for breaking the same, in which case the second component would be set to contain a second compound to be mixed instead of a vial for containing a second compound to be mixed.

In addition, in such case a cannula or a needle or double-flow perforator could be provided as illustrated with reference to the embodiment of FIGS. 22 and 23, set to place the first and the second housing zone in fluid communication, and such needle could for example be set to cross through the body of the second gasket, which, according to such variant, might not be annular or alternatively to cross through another separation element or component for the first and second housing zone.

Alternatively, the mixing group could provide for breaking or opening means, such as a stem or a punch, of a second gasket (not annular) or of a sealing or separation component or wall of the first and second housing zone.

Such needle or such breaking means could be supported by a portion of the first, second or third component and moved, for example manually, if desired by means of movement imparted to the component of the device associated with the needle or the breaking means.

For such purpose, a method according to the present invention could provide for, before the step of moving the second component with respect to the third component and/or the first component with respect to the third component, a step of perforating or breaking, if desired by means of a needle or cannula or a breaking means, the second gasket or a separation element or component for the first and second housing zone.

The invention claimed is:

1. A mixing group for mixing two compounds to obtain a mixture, such as bone cement or an acrylic resin or a hydraulic cement, comprising:
    a first component having a substantially tubular body and delimiting a first housing zone of a first compound to be mixed, said first component having a first end as well as a second end,
    a second component with substantially tubular body and delimiting a second housing zone, said second component having a third end as well as a fourth end, said second component being set to contain a second compound to be mixed or a vial for containing a second compound to be mixed,
    said first housing zone being in fluid communication with said second housing zone, so as to allow the passage of said second compound from said second housing zone to said first housing zone,
    said mixing group comprising:
    at least one third component with substantially tubular body arranged between said first end of said first component and said third end of said second component or surrounding said first end and said third end, said first component and said third component being slidable with respect to each other and said second component and said third component being slidable with respect to each other,
    as well as sealing means between said first component and said third component as well as between said second component and said third component,
    wherein said first component delimits a first channel in which said first housing zone is delimited, the volume of said first housing zone being variable as a consequence of the relative movement of said first component with respect to said third component, with said third component integral with said second component, or as a consequence of the relative movement of said second component with respect to said third component, with said first component integral with said third component.

2. The mixing group according to claim 1, wherein said sealing means comprise at least one first gasket arranged between said second component and said at least one third component as well as at least one second gasket between said first component and said at least one third component.

3. The mixing group according to claim 2, wherein said at least one among said at least one first gasket and said at least one second gasket is annular, and wherein said at least one first gasket is intended to ensure the sealed connection between said first component and said third component, whereas said at least one second gasket is intended to ensure the sealed connection between said second component and said third component.

4. The mixing group according to claim 3, wherein said at least one third component comprises a substantially cylindrical wall on one side defining a fifth end of said third component and on the other side supporting an annular wall defining a sixth end of said third component, and wherein said second component and said at least one third component are movable with respect to one another, between a first rest position in which said third end is proximal or in abutment on said annular wall and a second work position in which said third end is distal from said annular wall.

5. The mixing group according to claim 1, wherein said substantially tubular body of said at least one third component is at least partially mounted around said second component.

6. The mixing group according to claim 5, wherein said substantially tubular body of said at least one third component has a fifth end as well as a sixth end defining a passage opening that is substantially free so as to allow and not obstruct the passage of said second compound from said second housing zone to said first housing zone.

7. The mixing group according to claim 2, wherein said second gasket is fitted onto said third end of said second component and comprises a cylindrical main section with an end proximal to said third end and an end distal from said third end, said second gasket further comprising a first annular section protruding from said proximal end of said cylindrical main section towards the inside of said group or, in use, towards an axis of symmetry (x-x) of said group, so as to wrap around said third end.

8. The mixing group according to claim 7, wherein said second gasket comprises a second section protruding from said distal end of said cylindrical main section inside an annular recess delimited by said second component at said third end.

9. The mixing group according to claim 4, wherein in said first rest position a first annular section of said at least one second gasket is pressed between said third end and said annular wall.

10. The mixing group according to claim 1, wherein said third component delimits a second channel and wherein in said second channel a lung zone is delimited between said third component and said third end of said second component, the volume of said lung zone being variable following the relative movement of said second component and said third component.

11. The mixing group according to claim 10, wherein said second component and said third component are movable with respect to one another, between a first rest position and a second work position so as to increase the volume of said lung zone, this being obtainable by causing the sliding of said second component so as to bring said third end towards said fifth end of said third component.

12. The mixing group according to claim 1, wherein said first component and said third component are movable with respect to each other, between a first rest trim and a second work trim, so as to reduce said first housing zone.

13. The mixing group according to claim 1, comprising an abutment component fitted on said first end of said first component and intended to prevent the removal of said sixth end of said third component from a first channel delimited by said first component.

14. The mixing group according to claim 1, comprising at least one filler or through hole in fluid communication with said first housing zone and intended to be placed in fluid communication with suction means.

15. The mixing group according to claim 1, wherein said sixth end of said third component has a diameter or external section substantially corresponding to or slightly lower than a first channel delimited by said first component, so as to slide in and flush with the delimiting walls of said first channel.

16. The mixing group according to claim 1, wherein said third end of said second component has a diameter or external section substantially corresponding to a second channel delimited by said third component, so as to slide in and flush with the delimiting walls of said second channel.

17. The mixing group according to claim 2, wherein the coupling of said first gasket with said second component and with said at least one third component has a stability or resistance different with respect to the coupling of said second gasket with said first component and with said at least one third component, so that the seal between said second component and said at least one third component is different from the seal between said first component and said at least one third component.

18. The mixing group according to claim 2, wherein said at least one first gasket has hardness different from said second gasket.

19. A mixing group for mixing two compounds to obtain a mixture, such as bone cement or an acrylic resin or a hydraulic cement, comprising:
a first component having a substantially tubular body and delimiting a first housing zone of a first compound to be mixed, said first component having a first end and a second end comprising an opening for supplying the obtained mixture,
a second component with substantially tubular body and delimiting a second housing zone, said second component having a third end as well as a fourth end, said second component being set to contain a second compound to be mixed or a vial for containing a second compound to be mixed,
said first housing zone being in fluid communication with said second housing zone, so as to allow the passage of said second compound from said second housing zone to said first housing zone,
said mixing group comprising:
at least one third component with substantially tubular body arranged between said first end of said first component and said third end of said second component or surrounding said first end and said third end, said first component and said third component being slidable with respect to each other and said second component and said third component being slidable with respect to each other,
as well as sealing means between said first component and said third component as well as between said second component and said third component.

20. The mixing group of claim 19, wherein the second end comprises a hollow shank section extending from the opening.

* * * * *